United States Patent
Shinden et al.

(10) Patent No.: US 7,746,977 B2
(45) Date of Patent: Jun. 29, 2010

(54) DIGITAL RADIATION IMAGE RADIOGRAPHING SYSTEM

(75) Inventors: Yuko Shinden, Hino (JP); Hiromu Ohara, Shinjuku-ku (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 100 days.

(21) Appl. No.: 11/994,481

(22) PCT Filed: May 23, 2006

(86) PCT No.: PCT/JP2006/310178
§ 371 (c)(1),
(2), (4) Date: Jan. 2, 2008

(87) PCT Pub. No.: WO2007/007473
PCT Pub. Date: Jan. 18, 2007

(65) Prior Publication Data
US 2009/0116615 A1  May 7, 2009

(30) Foreign Application Priority Data

Jul. 8, 2005 (JP) ............................. 2005-199581
Jul. 8, 2005 (JP) ............................. 2005-199614

(51) Int. Cl.
*G01N 23/04* (2006.01)
(52) U.S. Cl. ....................................................... 378/62
(58) Field of Classification Search .................. 378/62, 378/98.8
See application file for complete search history.

(56) References Cited

U.S. PATENT DOCUMENTS 7,027,556 B2  4/2006  Ohara

| | | |
|---|---|---|
| 2001/0038707 A1 | 11/2001 | Ohara |
| 2003/0123611 A1 | 7/2003 | Ohara et al. |
| 2003/0215061 A1 | 11/2003 | Sakaida |
| 2004/0062349 A1 | 4/2004 | Shuster |
| 2004/0109530 A1 | 6/2004 | Amitani et al. |

(Continued)

FOREIGN PATENT DOCUMENTS

JP  2001-311701 A  11/2001

(Continued)

OTHER PUBLICATIONS

Related U.S. Appl. No. 11/915,841, filed Nov. 28, 2007, now abandoned.

(Continued)

*Primary Examiner*—Chih-Cheng G Kao
(74) *Attorney, Agent, or Firm*—Frishauf, Holtz, Goodman & Chick, P.C.

(57) ABSTRACT

A digital radiation image radiographing system includes an X-ray tube to irradiate a radiographic subject with X-rays and a digital detector to detect X-rays having passed through the radiographic subject, and performs a phase contrast radiography. The system satisfies a formula $(D \geqq (2S-E)/(M-1))$, in which D (μm) represents the focal size of the X-ray tube, S (μm) represents the minimum control unit of the digital detector, R1 (m) represents a distance from the focus point of the X-ray tube to the radiographic subject, R2 (m) represents a distance from the radiographic subject to the digital detector, M represents an enlargement ratio $(M=(R1+R2)/R1)$, and E represents an edge enhancement width according to X-ray refraction.

12 Claims, 12 Drawing Sheets

U.S. PATENT DOCUMENTS

| | | |
|---|---|---|
| 2005/0213801 A1 | 9/2005 | Ohara |
| 2005/0226376 A1 | 10/2005 | Yun et al. |
| 2005/0286680 A1 | 12/2005 | Momose |
| 2009/0080609 A1* | 3/2009 | Shinden et al. ............... 378/62 |

FOREIGN PATENT DOCUMENTS

| | | |
|---|---|---|
| JP | 2003-180670 A | 7/2003 |
| JP | 2004-208773 A | 7/2004 |

OTHER PUBLICATIONS

U.S. Office Action dated Jun. 11, 2009 issued in abandoned *related* U.S. Appl. No. 11/915,841.

Extended European Search Report dated Dec. 10, 2009 issued in counterpart European Application No. 06746712.

\* cited by examiner

ONE CONTROL UNIT WITH ONE PIXEL (= 1 X 1)

ONE CONTROL UNIT WITH FOUR PIXELS (= 2 X 2)

REFERENCE IMAGE DENSITY

MEASURED IMAGE DENSITY

IMAGE DENSITY DIFFERENCE = MEASURED IMAGE DENSITY - REFERENCE IMAGE DENSITY

| OUTPUTTING DEVICE ID | OUTPUT MODE | MINIMUM OUTPUT UNIT (µm) | |
|---|---|---|---|
| 104a | FILM RECORDING | 25 | 43.75 |
| 104b | FILM RECORDING | 27 | — |
| 104c | FILM RECORDING | 25 | 30.2 |
| 104d | MONITOR DISPLAY | 30 | — |
| 104e | MONITOR DISPLAY | 100 | — |

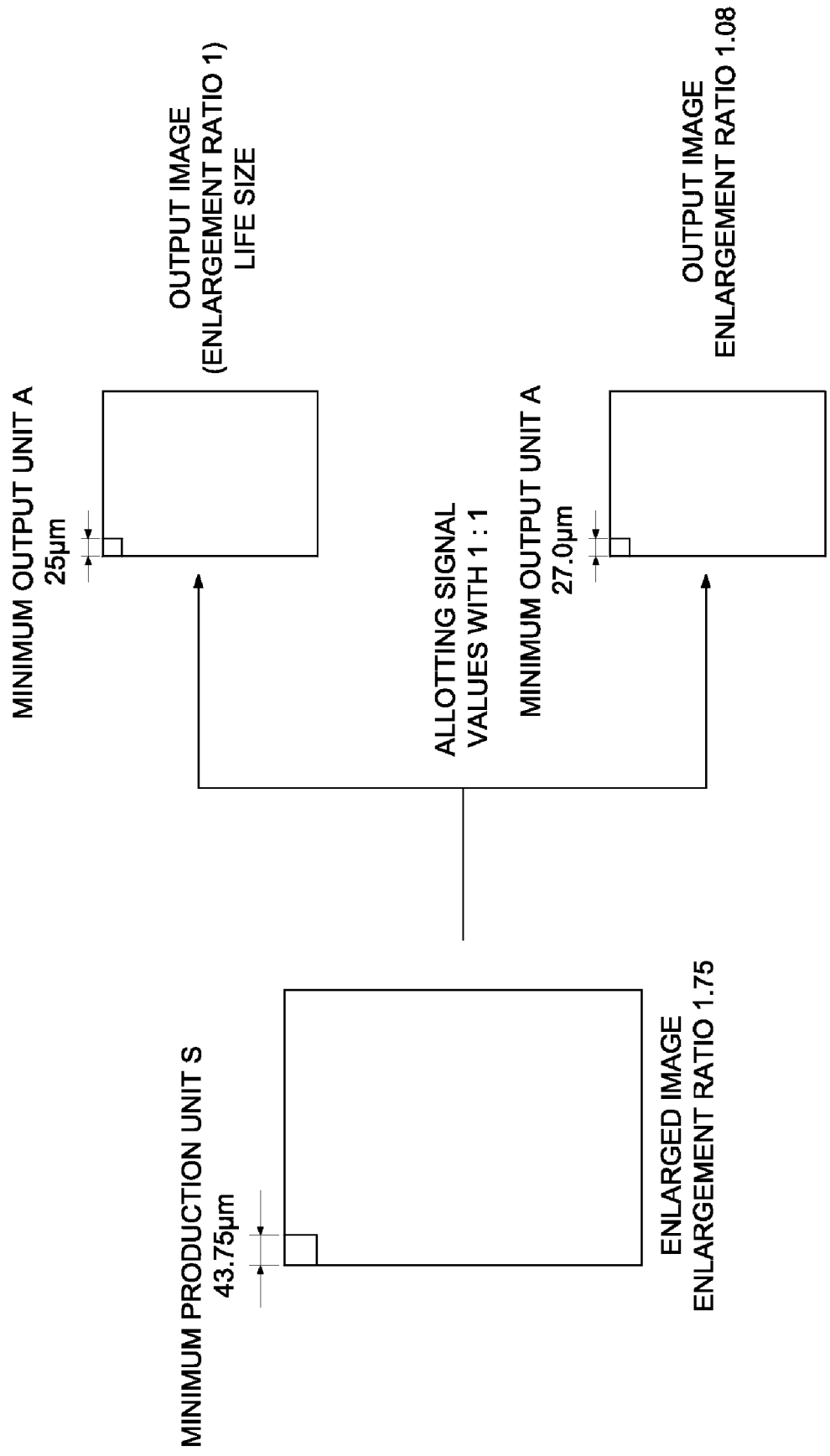

DIGITAL RADIATION IMAGE RADIOGRAPHING SYSTEM

This application is a U.S. National Phase Application under 35 USC 371 of International Application PCT/JP2006/310178 filed May 23, 2006.

TECHNICAL FIELD

The present invention relates to a digital radiation image radiographing system that radiographs a radiographic subject on a digital mode through a phase contrast radiographing method representing one of enlargement radiography, then, minifies digital image data (enlarged image of the subject) thus obtained to output them so that the image data may agree with a style of diagnosis (diagnosis based on an image whose size is substantially the same as that of the subject (which is called a life-size)) of a doctor for X-ray interpretation.

An image taken through a phase contrast radiographing method is an image with high visibility wherein a focus marginal section (contours) are subjected to edge enhancement, and it is highly expected in a medical field, and an improvement in diagnosis accuracy in a mammography (breast images) field is expected.

BACKGROUND OF THE INVENTION

Even in the field of medical images, the digitalization is advancing, and in the field of digital image radiographing, spatial resolution for reading images is restricted, depending on a reading pixel size of an X-ray detector or on a size of a reading sampling pitch. In this case, there are problems that a subject smaller than the reading pixel size or than the reading sampling pitch cannot be described and that a contour of the subject described turns out to be blurred even in the case of a subject larger than the reading pixel size or than the reading sampling pitch.

In addition, an X-ray detector becomes minute and complicated in terms of a structure, and a volume of data to be handled is increased, resulting in troubles that costs of memory for an X-ray detector and for data processing are increased and time required for data processing is increased.

Although the reading pixel size or the reading sampling pitch is important, it is impossible to achieve an improvement of visibility of a marginal section (contour) subjected to edge enhancement in an image (image used for diagnosis) to be presented finally to a doctor for X-ray interpretation, even if miniaturization alone for the reading pixel size or the reading sampling pitch is attempted.

Patent document 1 discloses a digital phase contrast X-ray image radiographing system provided with a digital-X-ray image detector to obtain a digital image of a phase contrast X-ray image in which the reading pixel size of this digital-X-rays image detector is almost equal to the phase contrast edge enhancement half band width of a phase contrast X-ray image.

Moreover, for example, when a phase contrast radiography is performed by the use of CR (Computed Radiography), FPD (Flat Panel Detector) an so on and thus obtained image data are outputted to a film or a viewer, if B=A/M in which M represents a photographing magnification at the time of phase-contrast radiography (magnifying power), A represents a minimum control unit (pixel size) at the time of reading and B represents a minimum control unit (pixel size) at the time of outputting, it may be possible to match a reading pixel and an output pixel with 1:1. In this case, since a reduction interpolating process becomes unnecessary, there has been well known no problem that a part of side edge image applied with an edge enhancement is disappeared at the time of interpolation treatment and image deterioration may not be caused

[Document 1] Japanese Patent Unexamined Publication No. 2003-180670

DISCLOSURE OF THE INVENTION

Problem to be Solved by the Invention

An image having an edge-enhanced side edge portion (boundary) on a characteristics range different from its periphery is obtained by this phase contrast radiography method as an image with a feature caused by this radiography. And, in order to output the image with good visibility on a film or a viewer, it is required to output faithfully the edge-enhanced side edge portion without destroying.

In the above-mentioned patent document 1, the image forming position of a peripheral zone of a disease portion on each minimum control unit of a detector, such as CR plate or FPD, there may be a case where a part of a mountain and a part of valley of output signals may reside together in the minimum control unit. In this case, since output signal values of a mountain and a valley are cancelled to each other, the output signal value in the concerned minimum control unit becomes low. Accordingly, a difference between an output signal values from a mountain and a valley and an output signal values from no mountain and no valley in the minimum control unit becomes smaller or they become the same level depending on the case. As a result, an edge-enhanced image cannot be acquired in the reading stage. After that, even if a faithfully reproducible output unit is used, an edge-satisfactory enhanced image cannot be acquired.

The present invention has been made in view of the above problems, and an object of the present invention is to provide a digital radiation image radiographing system, wherein when an image generated by the phase contrast radiographing method is read in digital mode, even if an image is formed at any phase (location) on each reading control unit, an edge being an effect of the phase contrast radiography can be certainly detected.

Means for Solving the Problem

The digital radiation image radiographing system of the present invention is a digital radiation image radiographing system which comprises an X-ray tube to irradiate a radiographic subject with X-rays and a digital detector to detect X-rays having passed through the above-mentioned radiographic subject and performs a phase contrast radiography, is characterized by being $(D \geq (2S-E)/(M-1))$, where D (μm) represents the focal size of the above-mentioned X-ray tube, S (μm) represents the minimum control unit of the above-mentioned digital detector, R1 (m) represents a distance from the focal point of the above-mentioned X-ray tube to the above-mentioned radiographic subject, R2 (m) represents a distance from the above-mentioned radiographic subject to the above-mentioned digital detector, M represents an enlargement ratio of $(M=(R1+R2)/R1)$ and E represents an edge enhancement width according to X-ray refraction.

Further, the digital radiation image radiographing system of the present invention is a digital radiation image radiographing system which comprises an X-ray tube to irradiate a radiographic subject with X-rays and a digital detector to detect X-rays having passed through the above-mentioned radiographic subject and performs a phase contrast radiography, is characterized by being $(D \geq 2S/(M-1))$, where D (μm)

represents the focal size of the above-mentioned X-ray tube, S (μm) represents the minimum control unit of the above-mentioned digital detector, R1 (m) represents a distance from the focal point of the above-mentioned X-ray tube to the above-mentioned radiographic subject, R2 (m) represents a distance from the above-mentioned radiographic subject to the above-mentioned digital detector, M represents an enlargement ratio of (M=(R1+R2)/R1) and E represents an edge enhancement width according to X-ray refraction.

Effect of the Invention

According to the present invention, when an image generated by the phase contrast radiography method is read in a digital mode, there is no case where a mountain and a valley of an edge are included in the same reading control unit. Therefore, even if an image is formed on any phase (location) for each reading control unit, edges which are an effect of the phase contrast radiography can be certainly detected.

BRIEF DESCRIPTION OF DRAWINGS

FIG. 18 shows a drawing indicating a relationship between an enlarged image and its output image, when the enlarged image and a minimum output unit are different from each other.

EXPLANATION OF NOTATION

Figure 1:
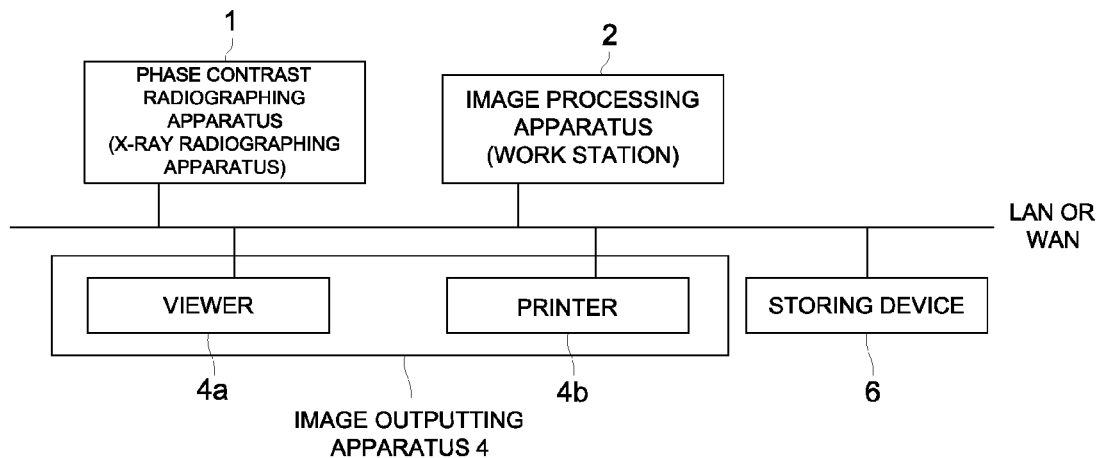
FIG. 1 shows a brief configuration of a digital radiation image radiographing system embodied in the present invention.

1 an X-ray radiographing apparatus
2 an image processing apparatus
4 an image output apparatus
4a a viewer
4b a printer
6 a preservation apparatus
100 a digital radiation image radiographing system
101a-101d image generating apparatuses
102 a JOB manager
103 a DB
104a-104c image recording apparatuses
104d-104e image displaying apparatuses

BEST MODE FOR CARRYING OUT THE INVENTION

First Example

FIG. 1 shows a digital radiation image radiographing system relating to the first embodiment. In the digital radiation image radiographing system in the present embodiment, phase contrast radiographing apparatus (X-ray radiographing apparatus) 1, image processing apparatus (work station) 2, image output apparatus 4 (viewer 4a, printer 4b) and preservation apparatus 6 are connected each other through LAN or WAN. Each apparatus is made to be possible for communication corresponding to DICOM protocol, and it reproduces digital image data generated by a phase contrast radiographing method.

First, in phase contrast radiographing apparatus 1, imaging for two-dimensional flat digital image is conducted, and after an X-ray image is taken through the aforesaid imaging, image signals are taken out and image processing is conducted by image processing apparatus 2. Further, image signals are subjected to image-display on viewer 4 of image output apparatus 4, and are subjected to image-print output with printer 4b.

The phase contrast radiographing apparatus 1 is preferably the so-called digital image radiographing apparatus, and it is provided with digital detectors such as CR, FPD and a division type X-ray detector. It may further be one that is taken through imaging on a screen or a film, and a film after developing is digitized by a digitizer.

FPD includes two types including the so-called a direct type and an indirect type, and these types are not restricted in the present invention. In the direct type FPD, X-ray are irradiated on a-Se, and electric charges thus generated are collected to be accumulated temporarily in a capacitor. Then, the accumulated electric charges are taken out in order on a two-dimensional basis, to be made image signals finally.

The division type X-ray detector includes one wherein image signals are taken out by causing CCD to touch directly a scintillator with a plane that emits visible light when it is irradiated by X-ray, one wherein image signals are taken out by collecting emitted light with a glass fiber and by leading it to CCD or the one wherein image signals are taken out by introducing emitted light to CCD by the use of a lens.

A reading pixel size or a reading sampling pitch of the digital detector is defined to be minimum control unit S (μm) in the case of reading. For the minimum control unit S, ($10 \leq S \leq 200$ μm) is preferable If S is greater than 200 μm, it is difficult to acquire precisely X-ray image transmitted through a subject, while, if it is smaller 10 μm, an yield rate is worsened and manufacturing cost is increased. More preferable is ($30 \leq S \leq 100$ μm), and by conducting reading sampling in this area, it is possible to read without lacking an edge-emphasized boundary image obtained through phase contrast imaging, and sharpness is improved.

Viewer 4a is used to display imaged data and to check the quality of positioning of imaging region. When it is satisfactory, an engineer transmits the aforesaid data to preservation apparatus 6 such as a storage apparatus to preserve them. Further, simultaneously with this, the aforesaid image data may also be transmitted to an unillustrated work station for a doctor for X-ray interpretation.

A cathode ray tube (CRT), a liquid crystal, a plasma-display, a liquid crystal projector and organic EL can be used as the viewer 4a. In the viewer 4a, luminance: 400-1000 cd/m$^2$, contrast ratio: 200-10000, and depth of information: 8 or 16 bit are preferable. Though a size of an image plane is not restricted in particular, a size that can cover the whole of the region to be imaged is preferable. It is preferable that the name of a patient, a magnification rate for imaging and character information such as a date of imaging are displayed together with images. Further, the past image, other modality images such as X-ray CT and MRI, resection test body images and color images such as fundus images may also be displayed simultaneously or separately.

An output pixel size of the viewer 4a or an output writing pitch of printer 4b is defined to be minimum control unit A (μm) in the case of outputting.

Figure 2:
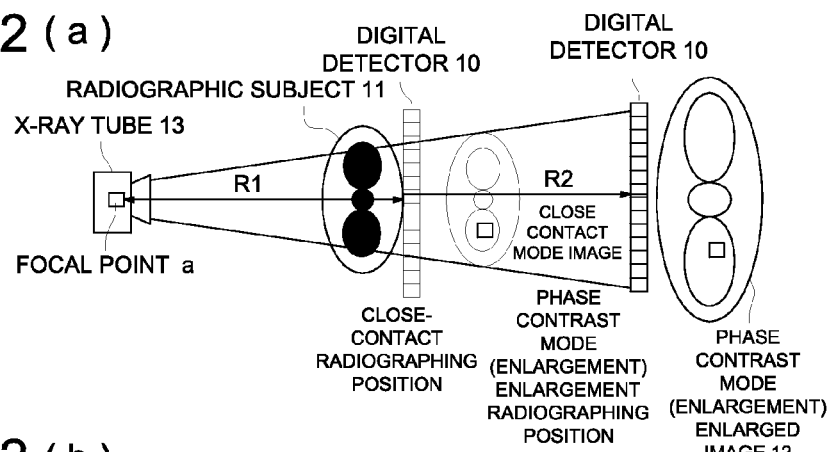
FIG. 2(a) and FIG. 2(b) show brief configurations of X-ray radiographing apparatus embodied in the present invention.
Figure 2:
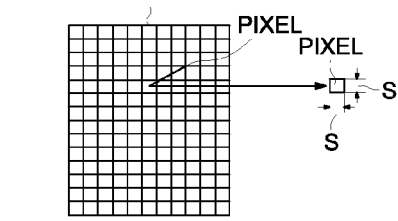

Next, a phase contrast radiographing method will be explained based on FIG. 2. FIG. 2 shows an outline of X-ray radiographing apparatus 1 shown in FIG. 1. Contact imaging means imaging under the state where subject 11 is in contact with digital detector 10 or with a member including the digital detector 10. A distance from the position of subject 11 on the digital detector 10 side to the digital detector 10 or to the member including that is defined to be R2. The contact imaging means that R2 is 0 or it is substantially 0. A meaning of the expression that R2 is substantially 0 is that R2 is not more than 0.05 m, or magnifying power M is less than 1.1. The magnifying power M is defined to be a value obtained by dividing the maximum length of a projected image by a length of a corresponding portion of a main body of the subject.

A phase contrast image is obtained by selecting the magnifying power M of ($1 < M \leq 10$). A range of ($1.4 \leq M \leq 3$) is preferable, and by selecting the magnifying power M of this range, a phase contrast image having high image quality usable as an image for diagnoses can be obtained.

When digital detector 10 is installed to be away from subject 11 as shown in FIG. 2, it is possible to obtain phase contrast image 12 through imaging by X-rays emitted from X-ray tube 13. An occasion where R2 exceeds 0.05 m and an occasion where the magnifying power M is not less than 1.1 mean the phase contrast imaging.

A range of distance R1 between focal point a of X-ray tube 13 of the present embodiment and subject 11 is ($0.15 \leq R1 \leq 5$ m) when a form of an ordinary imaging room (especially, a distance between a floor and a ceiling) and a thickness of a subject are taken into consideration, and it is preferably ($0.25 \leq R1 \leq 2$ m) when image quality and work efficiency are further considered. Further, a range of distance R2 between subject 11 and digital detector 10 subject 11 is ($0.15 \leq R2 \leq 5$ m) when a form of an ordinary imaging room (especially, a distance between a floor and a ceiling) and image quality that makes a diagnosis possible are taken into consideration, and it is preferably ($0.5 \leq R2 \leq 2$ m).

A rotation anode hot-cathode tube is preferable as X-ray tube 13. Namely, in the rotation anode hot-cathode tube, an electron is emitted from a filament, then, the electron hits the anode on which optional voltage in a range from 10 kV to 500 kV is applied, and kinetic energy of the electron is converted into an electromagnetic wave to be emitted as X-ray. In this case, a carbon nanotube may be used as one that emits electrons, although a filament may also be used. It is preferable that the anode is made of a metal of molybdenum or tungsten, and it is rotated so that it may not be damaged by generation of heat caused by a collision of a thermoelectron. A form of the portion where the thermoelectron hits the anode is usually designed to be a perfect square when it is viewed in the direction of the emission, and it is called a focal point A length of one side of this perfect square is called focal point diameter D which indicates a size of an X-ray source. The focal point diameter D is one to be shown generally by a manufacturer of X-ray tube as a specification, and it can be measured by using a pin-hole camera or a test chart as is established in JIS Z4702.

A range of the focal point diameter D is ($1 \leq D \leq 300$ μm) and it is preferably ($30 \leq D \leq 100$ μm). By selecting the focal point diameter D of 1 μm or more, an output of X-ray just for being transmitted through subject 11 is obtained, and an image having high image quality suitable for a diagnosis can be obtained by selecting the focal point diameter D of 30 μm or more. If the focal point diameter is small, a period of time for imaging is long although image quality is improved. Since a form of a structure having a size of about 100 μm needs to be observed in the case of mammography, the focal point diameter is in a range from 30 μm to 100 μm because a smaller focal point is desired. By selecting the focal point diameter D in a range of ($30 \leq D \leq 100$ μm), an edge image which can be detected by digital detector 10 can be obtained, and an image with high sharpness can be obtained.

A range of minimum control unit S (μm) representing a reading pixel size of digital detector 10 or a reading sampling pitch is ($10 \leq S \leq 200$ μm) and it is preferably ($30 \leq S \leq 100$ μm). The smaller the minimum control unit S is, the more precise image is obtained and details of the structure can be observed. However, manufacturing of the detector becomes difficult, and an yield rate of products is lowered. It is preferable that an area of detection by digital detector 10 covers the total area where a subject region is enlarged.

A range of minimum control unit A representing an output pixel size of image outputting apparatus 4 or an output writing pitch is ($25 \leq A \leq 300$ μm), and when the minimum control unit A is too large, a contour of an image is blurred, while, when it is smaller, a precise image can be displayed, and it is possible to observe up to details of the structure. However, when the minimum control unit A is small, a manufacturing yield is worsened and manufacturing cost is increased. Further, an amount of image data grows greater, and it takes longer time for display and switching of images, resulting in a decline of work efficiency.

The preferable range is ($50 \leq A \leq 200$ μm), and when 200 μm is exceeded, it sometimes is difficult to diagnose in the case of precise diagnosis such as observing a minute structure.

Phase contrast radiographing apparatus 1 is an apparatus that conducts imaging in the aforesaid method, and utilizes a phenomenon wherein an edge is generated on the circumference of an image of a subject by refraction of X-ray, to acquire a radiation image having higher sharpness.

Figure 3:
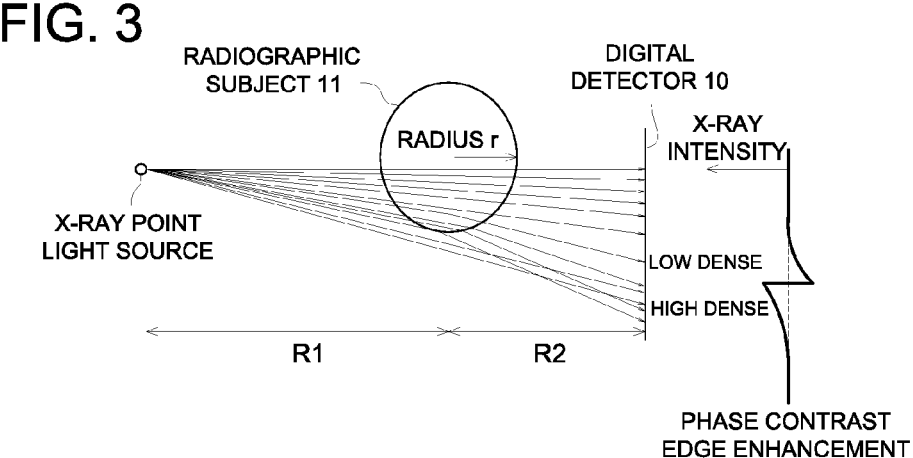
FIG. 3 shows an explanatory drawing for explaining a principle how to generate a phase contrast edge enhancement of a subject image due to deflections of X rays.

In the phase contrast imaging, an X-ray passing through the circumference of subject 11 is refracted and overlaps with X-ray having passed through a flank of subject 11 on digital detector 10, outside the circumstance of subject 11, as shown in FIG. 3, and intensity of X-ray is strengthened. On the contrary, in the vicinity of the inside of the circumstance of subject 11, X-ray intensity is weakened. As stated above, with respect to the X-ray intensity, a peak is caused on the outside and trough is caused in the inside, with the circumference of subject 11 serving as a boundary, thus, an edge is emphasized. This edge enhancement function is also called an edge effect. Owing to this edge enhancement function, an X-ray image having excellent sharpness whose circumstance is described clearly can be obtained.

Figure 4:
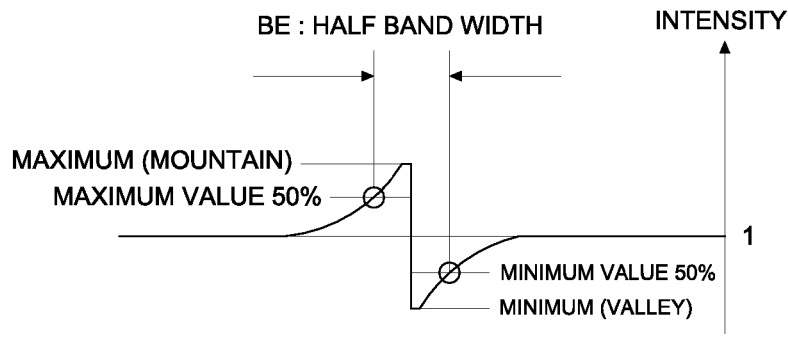
FIG. 4 shows a graph indicating a half band width of the phase contrast edge enhancement.

In this case, as shown in FIG. 4, if the X-ray source is regarded as a point source of light, half-width E of phase contrast edge enhancement can be expressed by the following expression (1);

$$E=2.3(1+R2/R1)^{1/3}\{R2\delta(2r)^{1/2}\}^{2/3} \quad (1)$$

wherein, $\delta$ represents a refractive index difference at the portion where X-ray is refracted and r represents a radius of an object (or a subject, a photographic subject).

Figure 5:
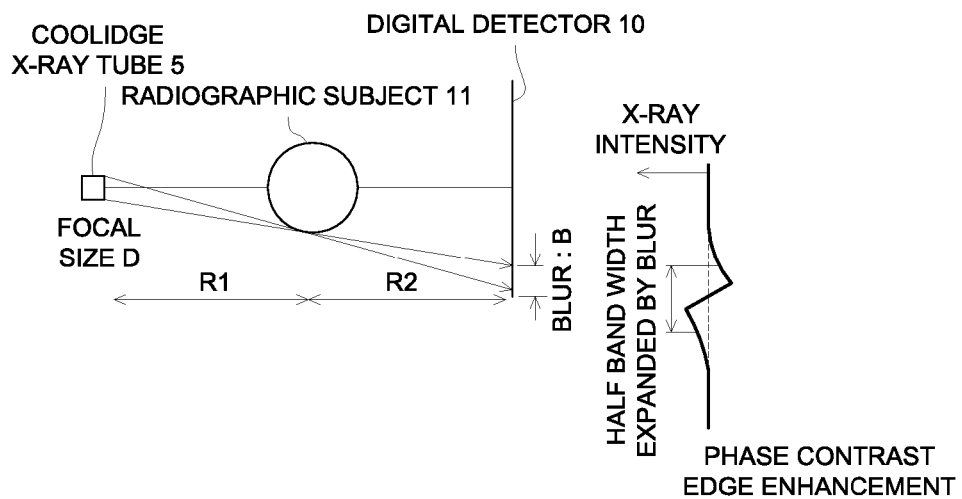
FIG. 5 shows a graph indicating a half band width of the phase contrast edge enhancement when employing a Coolidge X-ray tube.
Figure 6:
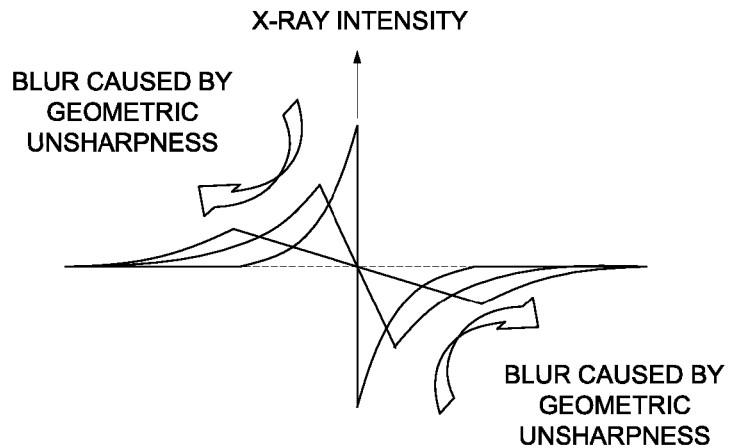
FIG. 6 shows an explanatory drawing for explaining a fact that a pixel size of a digital detector is detectable even if it has a predetermined dimension.
Figure 7:
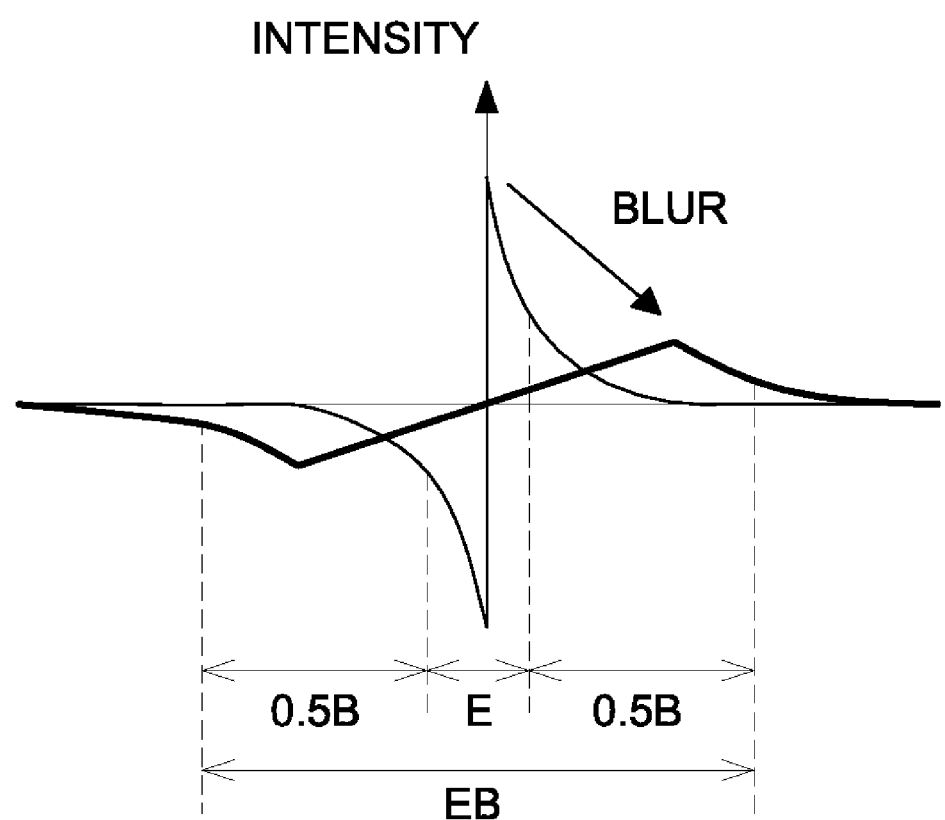
FIG. 7 shows an explanatory drawing for explaining a fact that, due to geometric unsharpness, an edge enhancement width is widened to such a width that is wider than that created by X rays emitted from an ideal point light source.

On the other hand, in the medical job site and in the non-destructive inspection facility, Coolidge X-ray tube 5 (which is also called thermoelectron X-ray tube) is widely used. FIG. 5 shows an occasion where Coolidge X-ray tube 5 is used. In the Coolidge X-ray tube 5, a thermoelectron hits the anode made of metal such as tungsten to emit X-ray, and X-ray is emitted radially from a window in a form of a perfect square which is called a focal point. A length of one side of this window in a form of a perfect square is called focal point diameter. When using Coolidge X-ray tube 5, an X-ray source cannot be regarded as an ideal point light source. Namely, by a focal point serving as an X-ray source having a finite size, half-width E for phase contrast edge enhancement is broadened by the so-called geometric unsharpness as shown in FIG. 6, and intensity is decreased. In this case, half-width E for phase contrast edge enhancement can be expressed by the following expression (2), $$EB=2.3(1+R2/R1)^{1/3}\{R2\delta(2r)^{1/2}\}^{2/3}+D(R2/R1) \quad (2)$$

wherein D represents a focal point diameter of Coolidge X-ray tube 5 to be used.

When using Coolidge X-ray tube 5, half-width E for phase contrast edge enhancement is broadened by the so-called geometric unsharpness, and an edge enhancement image is blurred. However, on the contrary, detection of an edge enhancement image is possible even when a pixel size of digital detector 10 is relatively large, because half-width E is broadened.

For providing a highly sharp image obtained by phase contrast imaging as an image for diagnosis, an edge-emphasized image needs to be detected accurately firstly, and image information of the detected edge-emphasized image needs to be outputted under the diagnosable state without being lost secondly.

Figure 8A:
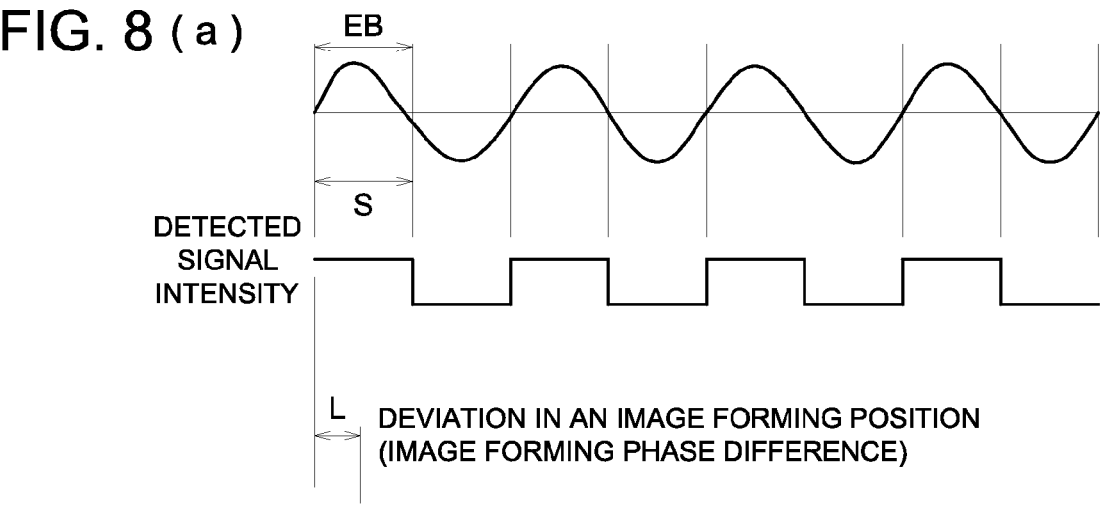
FIG. 8 shows a drawing for explain that there may case where edges are not recognized although edges may be always recognized by sampling with a reading sampling pitch same with the half band width EB.
Figure 8B:
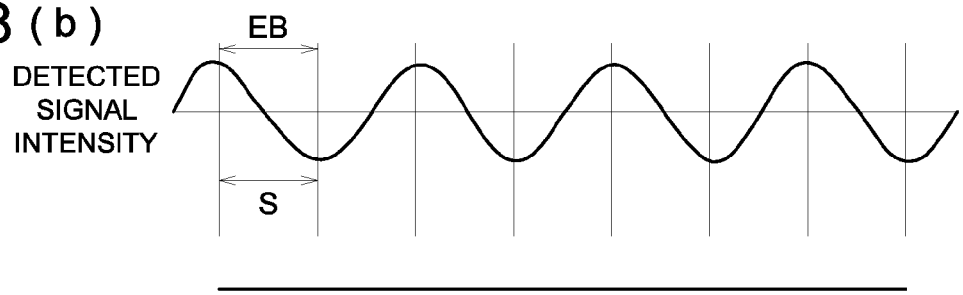
Figure 8C:
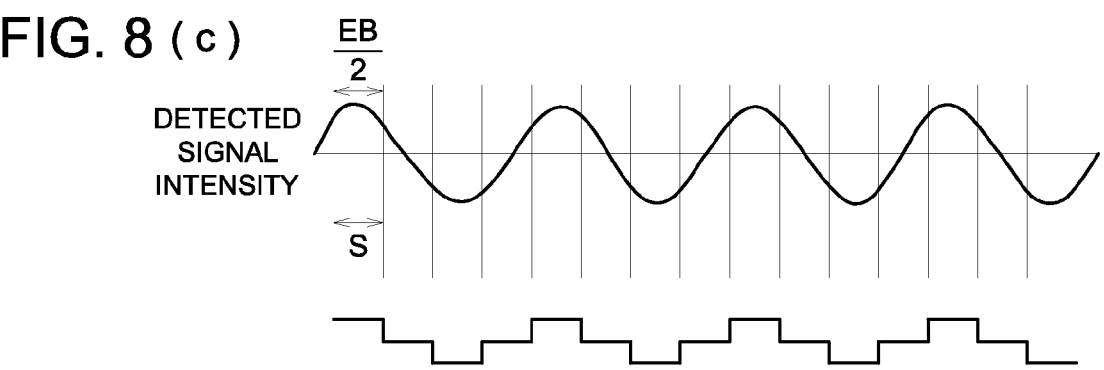

First, detection will be explained. An edge enhancement half-width obtained by a phase contrast radiographing method is indicated with (EB=E+B) as shown in FIG. 8. E represents an edge enhancement width formed by X-rays emitted from a point light source whose X-ray source of X-ray tube is ideal. B represents a size of blur caused by geometric unsharpness. Edge enhancement width EB by X-rays emitted from a light source having focal point diameter D is broadened by geometric unsharpness to be more than edge enhancement width E formed by X-rays emitted from an ideal point light source. ES represents edge enhancement half-width, and it indicates a distance between a peak of the edge and a trough, and is expressed by (E+B) wherein blur B is added to ideal edge enhancement width E.

When EB is smaller than a minimum control unit S (reading pixel size or reading sampling pitch), the visibility of edge enhancement becomes low. And, depending on the conditions, the probability that an image becomes invisible may become higher.

This is caused by the fact that since EB is smaller than S, the mountain and valley of an edge are included in the same reading minimum control unit and a part or all of them is offset or get balanced out.

When EB is smaller than S, depending on an edge image forming position for the reading minimum control unit, there may be a case that a mountain and valley of edge are caught in respective separate control units, and an image with which edge enhancement is visible may be acquired. However, whether or not an edge image forming position is located properly on the reading minimum control unit is determined probabilistically. Therefore, even when an image is radiographed with the same radiographing condition, there may be a case where an edge is not visible or another case where an edge can be seen. The probability that an edge can be seen becomes higher when EB is larger in comparison with S, and an edge always becomes visible when EB is larger than a certain magnitude.

When an X-ray image having passed through a radiographic subject is taken by a digital detector, it is necessary to satisfy a sampling theorem.

The sampling theorem is a theorem referred to that when the maximum spatial frequency which an analog image has is fmax (cycles/mm), it is necessary to set a sampling interval $\Delta x$ (mm) to ($\Delta x \leq 1/(2fmax)$).

If the above is expressed with a concrete value, for example, when the maximum spatial frequency which an analog image has is 5 cycles/mm, it is necessary to digitize with a sampling interval of 0.1 mm or less.

Now, assuming an image in which a width 2EB obtained by the addition of the mountain and valley of edge is a period of the maximum spatial frequency (fmax) which the image has, if the above-mentioned sampling theorem is applied to this image, it is possible to obtain a sampling interval required to detect an edge by a digital detector.

At this time, the maximum spatial frequency fmax is expressed with the formula (fmax=1/(2EB) (cycles/mm)). Therefore, a sampling interval $\Delta x$ required to reproduce an edge is ($\Delta x <= EB$ (mm)), and if a reading width is below an edge enhancement half band width EB, a mountain and valley of an edge can be detected (FIG. 8 (a)).

However, when a sampling is conducted with a reading minimum control unit S having the same size as an edge enhancement half band width EB, although a probability is low, if the relationship between each reading minimum control unit S and an image formation position (phase) becomes as shown in FIG. 8 (b) (deviate by (L=S/2) for FIG. 8 (a)), since signal values read each reading minimum control unit S become the same intensity (or although there is an output intensity difference, the difference is such a intensity difference being too small to be invisible for by human being's eyes), an edge cannot be recognized with the detected signal value.

Therefore, in order to recognize an edge, it is necessary to be (S<EB), and when an edge is needed to be detected more certainly, it is desirable to be (S≦EB/2) (FIG. 8 (c)).

On the other hand, since blur B due to geometric unsharpness can be obtained by (B=D (M−1)), the following formula (3) can be obtained with (S≦EB/2), i.e., (S≦(E+B)/2).

$$D \geq (2S-E)/(M-1) \qquad (3)$$

In this embodiment, under the assumption that D (μm) represents a focal point diameter of X-ray tube, S (μm) represents a minimum control unit (reading pixel size or reading sampling pitch) of a digital detector, R1 (m) represents a distance from a focal point of X-ray tube to a subject, R2 (m) represents a distance from a subject to a digital detector, a magnifying power M equals ((R1+R2)/R1) and E represents an edge enhancement width caused by X-ray refraction, the following formula is obtained.

$$D \geq (2S-E)/(M-1)$$

As mentioned above, an edge can be certainly detected, if a radiation image radiographing system is made to become (D≧(2S−E)/(M−1)).

Figure 9:
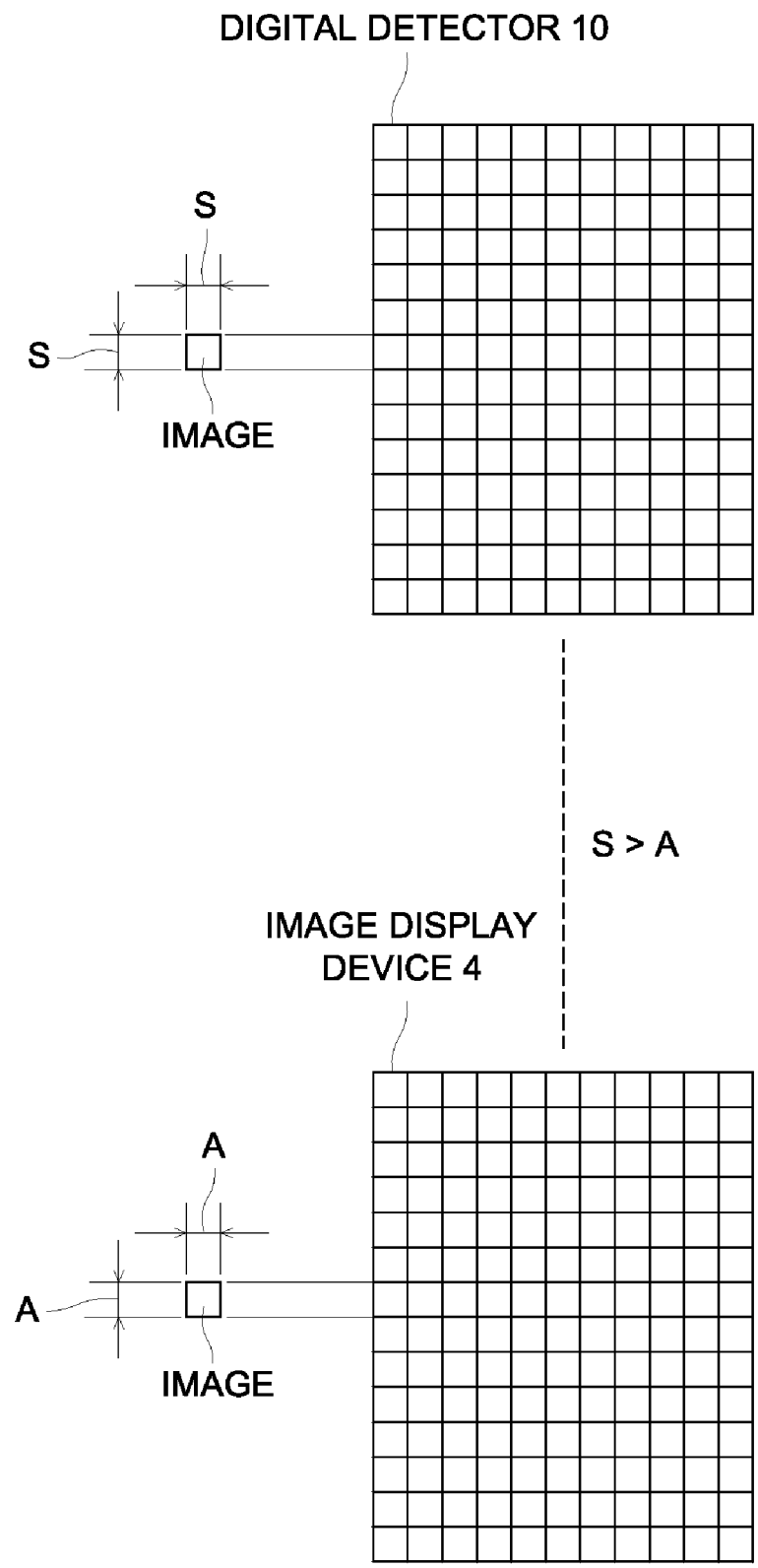
FIG. 9 shows a drawing indicating a relationship between a minimum control unit (reading pixel size, or reading sampling pitch) "S" at a digital detector and another minimum control unit (output pixel size, or output writing pitch) "A" of an image output apparatus.

Next, an output will be explained. A detected image becomes an image enlarged rather than the exact size by carrying out a phase contrast radiography. Therefore, as shown in FIG. 9, when a minimum control unit S (a reading pixel size or a reading sampling pitch) in a digital detector 10 is made to correspond to a minimum control unit A (an output pixel size or an output writing pitch) of an image outputting apparatus 4, since it is necessary to reduce an image to a full scale, it is necessary to be (S>A).

Figure 10A:
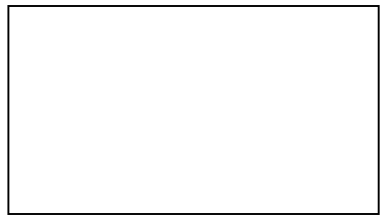
FIG. 10(a) and FIG. 10 (b) show explanatory drawings for explaining a control unit.
Figure 10B:
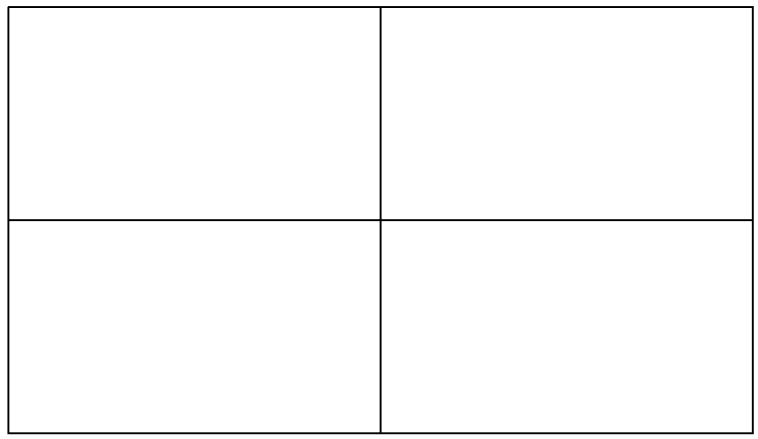

At this time, the minimum control unit S of the digital detector 10 and an aggregation of n pieces of the minimum control unit A of the image outputting apparatus 4 are corresponded as data (an image density value or a luminance value calculate based on an amount of transmission X rays of each of the minimum control unit S of the digital detector 10 is allotted as output data of the n pieces of the minimum control unit A of the image outputting apparatus 4). As shown in FIG. 10 (a), there may be a case that one pixel being the physical resolution of the image outputting apparatus 4 is allotted as one control unit to the minimum control unit S of the digital detector 10 (corresponding to n=1), or as shown in FIG. 10 (b), there may be a case that plural pixels of m×n (for example, (2×2=4) pixels (corresponding to n=4)) is allotted as one control unit. When plural pixels are allotted, the output value of each pixel is averaged and the averaged value is treated as an output value of the concerned region. When the both control units are similar figures, the both control units are made a minimum control unit having the same number (m=n) in longitudinal and transverse, and when the both control units are not similar figures, it becomes (m≠n, m is not equal to n).

With this way, a reduction interpolating process becomes unnecessary, an edge enhancement image is not disappear in connection with a reduction interpolating process, and good visibility will be acquired in the boundary section to which edge enhancement is carried out. In particular, the magnification is also in agreement, when an enlargement ratio is M, if conditions are made to be (S=MA) and (n=1), it is possible to output in life size.

Although it is considered as (EB=E+B) in the above-mentioned embodiment, in the focal size and the radiographing condition being used for general medical-use radiographing apparatus, since most of them are a blur width B (the blur width B being from several times to several ten times of an ideal edge enhancement half band width E), the edge enhancement half band width EB may be approximated with (ES=B).

When (EB=B), it is set to (S≦B/2), and from (B=D(M−1)), it is set to the formula (4)

$$D \geq 2S/(M-1) \qquad (4)$$

In this case, as same as the case of the above-mentioned embodiment, an edge can be certainly detected. Moreover, with regard to an output, it is the same as that of the case of the above-mentioned embodiment.

Example of a Radiography Experiment

An evaluation was conducted in such a way that a cylindrical plastic fiber with a radius of 1 mm was radiographed as a radiographic subject, and an image was printed with the imager having a minimum control unit A in a range of (25 μm≦A≦300 μm). The degree of edge enhancement was observed by the scanning of 20 points on edge portions of the printed image with a microdensitometer for each condition.

The radiography experiment was conducted on the radiographing conditions of an X-ray energy of 50 KeV, an X ray irradiation amount of 50 mAs, an enlargement ratio of (M=1.75 (R1=1 m, R2=0.7 m) and an enlargement ratio of (M=2 (R1=1 m, R2=1 m).

As a used X-ray source employed was a nondestructive inspection-use X-ray source modified such that a focal size D can be changed from 18 μm to 300 μm on account of setting a required focal size. A rotating anode-type tungsten tube was used as a target (anode) of an X-ray tube. In this connection, a focal size is an actually-measured size and is not an indication size.

As a digital detector used was a cassette type direct digitizer: Regius MODEL 190 manufactured by Konica Minolta Co., Ltd. which is CR. In this digital detector, a reading sampling pitch (a reading minimum control unit S) was selectable from two kinds of 43.75 μm and 87.5 μm.

As an outputting device used was a laser imager: DRYPRO MODEL793 manufactured by Konica Minolta Co., Ltd. In this outputting device, an output writing pitch (an output minimum control unit A) was selectable from two kinds of 25 μm and 43.75 μm. And each digital data obtained with the reading sampling pitch of the digital detector was matched with data of the output writing pitch by 1:1, and a film output was performed.

The range of D of the focal size in the formula (3) and the Formula (4) was as follows.

At the time of (d=8×10−7), (r=0.001 m), (M=1.75), (E=24.9 μm), and (S=43.75 μm), it was (D≧83.58 (Formula (3)) and (D≧116.67 (Formula (4)).

At the time of (d=8×10−7), (r=0.001 m), (M=1.75), (E=24.9μ), and (S=87.5 μm), it was (D≧200 (Formula (3)) and (D≧233 (Formula (4)).

At the time of (d=8×10−7), (r=0.001 m), (M=2), (E=31.46 μm), and (S=87.5 μm), it was (D≧143 (Formula (3)) and (D≧175 (Formula (4)).

Figure 11:
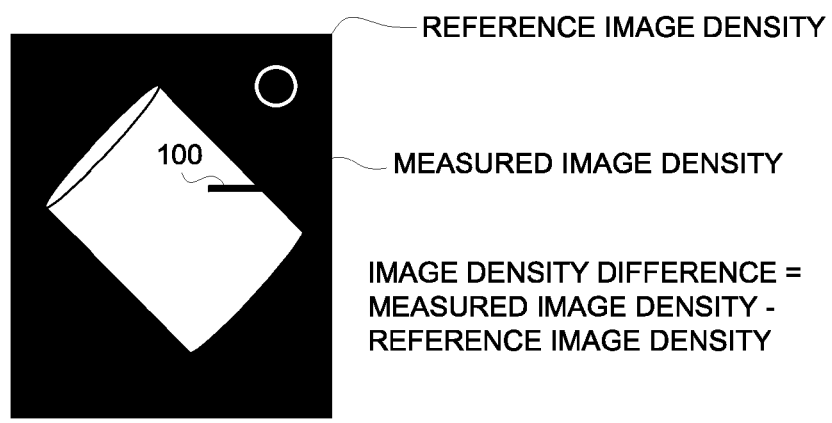
FIG. 11 is an illustration showing a model of a plastic fiber image.

FIG. 11 shows an example of a plastic fiber image.

An image density of the fiber image was measured by the scanning on line-segment 100 shown in FIG. 11 with a microdensitometer. Also, an image density of an uniform exposure section was measured as a reference image density. An image density difference was obtained by the subtraction to subtract the reference image density from the measured density of a fiber image.

Figure 12:
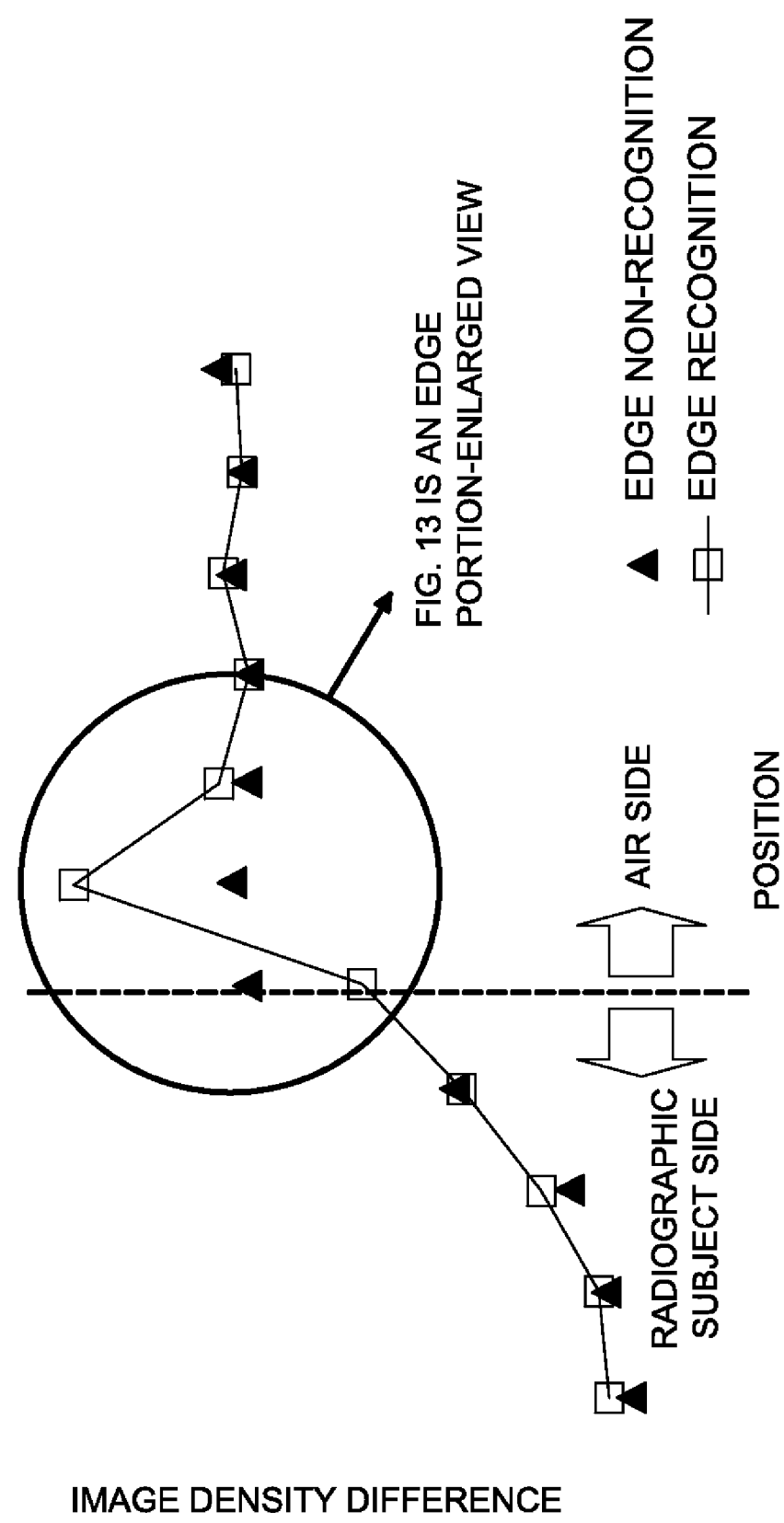
FIG. 12 a schematic diagram showing a relationship between a density difference obtained by subtracting a reference image density from an image density of a fiber image and a position.

FIG. 12 shows an example of a result of the obtained image density difference. On an image outputted to a film, in the case that an edge is clearly visible, a graph having a shape indicated with "edge having recognized" shown in FIG. 12 may be obtained. That is, a graph in which a peak is seen near an interface between a radiographic subject side and an air side may be obtained. With the lowering of the visibility of an edge, a peak on a graph becomes lower. In the case that an edge is invisible, a graph having a shape indicated with "edge having not recognized" shown in FIG. 12 may be obtained.

Moreover, in an image in which an edge is recognized at a time or is not recognized at another time, if the measurements on 20 points are averaged, the height of an edge enhancement peak becomes low.

Figure 13:
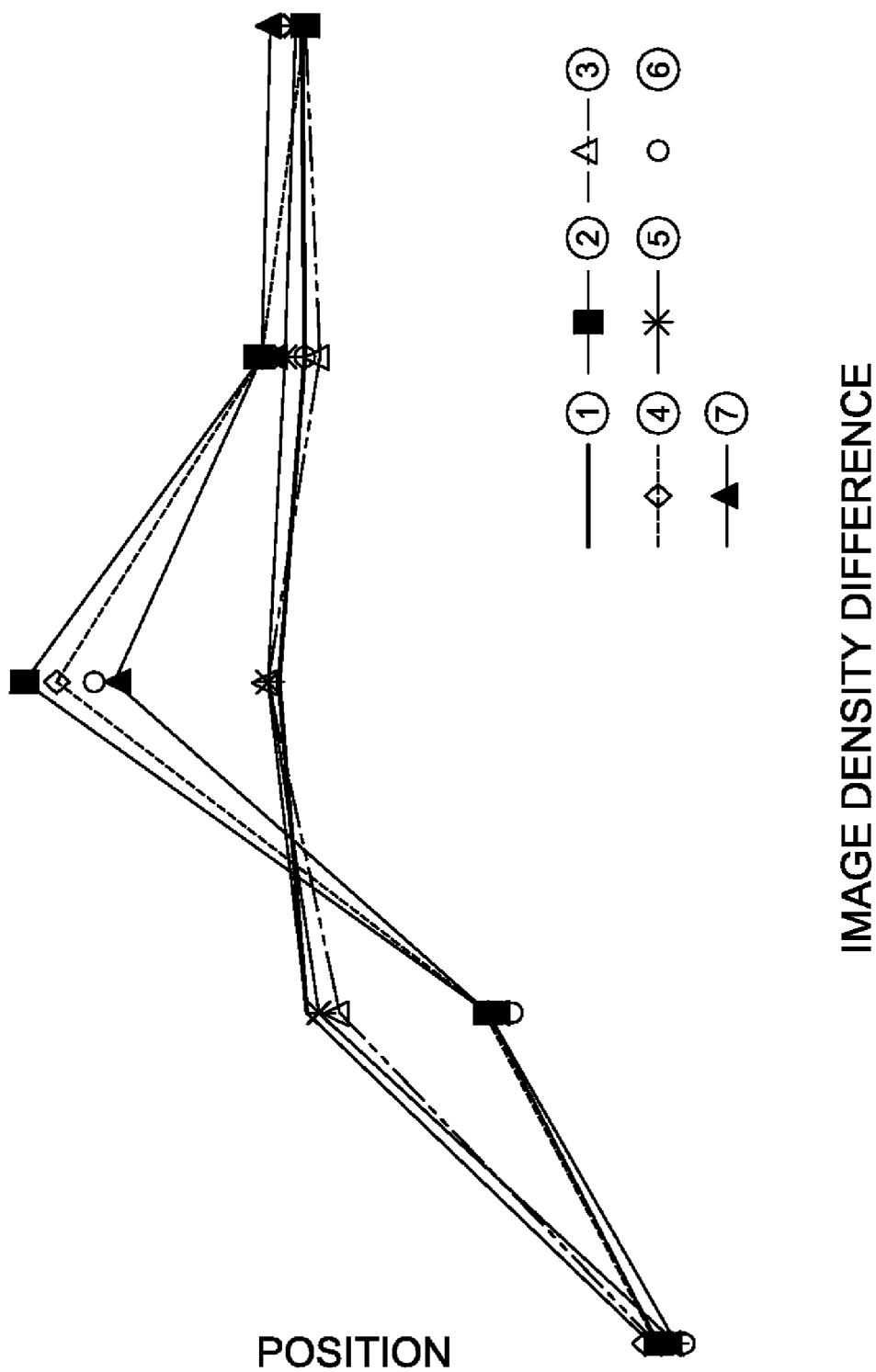
FIG. 13 is an enlarged view of an edge portion shown in FIG. 12.

FIG. 13 shows measurement results in this radiography experiment example and is an enlarged view of an edge portion corresponding to the portion surrounded with a circle shown in FIG. 12. The experimental conditions are shown in Table 1. A symbol □ shows the case where Formula (3) and Formula (4) were satisfied, and a symbol ■ shows the case where they were not satisfied.

In an experiment using a plastic fiber like this experiment, it is possible to apply a formula (3) so as to specify the relationship among D, A, S, and M. However, in the case where a living body is actually radiographed, since various compounds are mixed and a configuration is also complicated, a calculation employing Formula (3) may be difficult. In contrast, since Formula (4) is a formula which uses only values determined by the set-up of an apparatus, not a radiographic subject, a calculation is simple and is practical.

In this case, since the result depended on Formula (4) which approximates (S−E) as S can be obtained as a result almost equal to the result depended on Formula (3), it may be understood that it may be better to use Formula (4) for a practical use.

As mentioned above, according to the present invention, when an image generated by the phase contrast radiography method is read in a digital mode, there is no case where a mountain and a valley of an edge are included in the same reading control unit. Therefore, even if an image is formed on

TABLE 1

| | Focus size D [μm] | Detector reading pitch S [μm] | Enlargement ratio M | Output writing pitch A [μm] | Relationship with Formula (3) | Relationship with Formula (4) | Judgement |
|---|---|---|---|---|---|---|---|
| Measurement example 1 | 50 | 43.75 | 1.75 | 25 | ■ | ■ | Bad |
| Measurement example 2 | 100 | 43.75 | 1.75 | 25 | □ | □ | Good |
| Measurement example 3 | 100 | 87.5 | 2 | 43.75 | ■ | ■ | Bad |
| Measurement example 4 | 300 | 87.5 | 2 | 43.75 | □ | □ | Good |
| Measurement example 5 | 100 | 87.5 | 1.75 | 43.75 | ■ | ■ | Bad |
| Measurement example 6 | 300 | 87.5 | 1.75 | 43.75 | □ | □ | Good |
| Measurement example 7 | 200 | 87.5 | 1.75 | 43.75 | □ | ■ | Good |

As being clear from Table 1, in the cases (measurement examples 2, 4, 6, and 7) where Formula (3) was satisfied, even if it is a radiographic subject as shown in FIG. 11 in which side edges of the plastic fiber were arranged (with a slanting arrangement) on image forming positions with various phases for each reading control unit of the digital detector, clear edges with high intensity were observed continuously on each ridgeline (side edge) of the plastic fiber regardless the size of write-in pitch. On the other hand, in the cases (measurement examples 1, 3, and 5) where Formula (3) was not satisfied, edges were not observed.

This is because images having a phase contrast effect (edge enhancement) on a peripheral zone were detected with high intensity in digital mode at the reading step by the digital reading section (detector) of this invention.

Even if the reading sampling pitch S, the output writing pitch A, and the focal size D were changed, this inclination was not changed.

Also, in the cases (measurement examples 2, 4, and 6) where Formula (4) was satisfied, clear edges with high intensity were observed. Even in the case such as measurement example 7 where Formula (4) was satisfied, edges were observed. It is because Formula (4) is limited more narrowly than Formula (3), the range of Formula (4) locates always within the range of Formula (3). In the measurement example 7, as mentioned above, Formula (3) was satisfied.

any phase (location) for each reading control unit, edges which are an effect of the phase contrast radiography can be certainly detected. As a result, the edge visibility in a final output image (a film or a viewer) can be improved.

Second Embodiment

Figure 14:
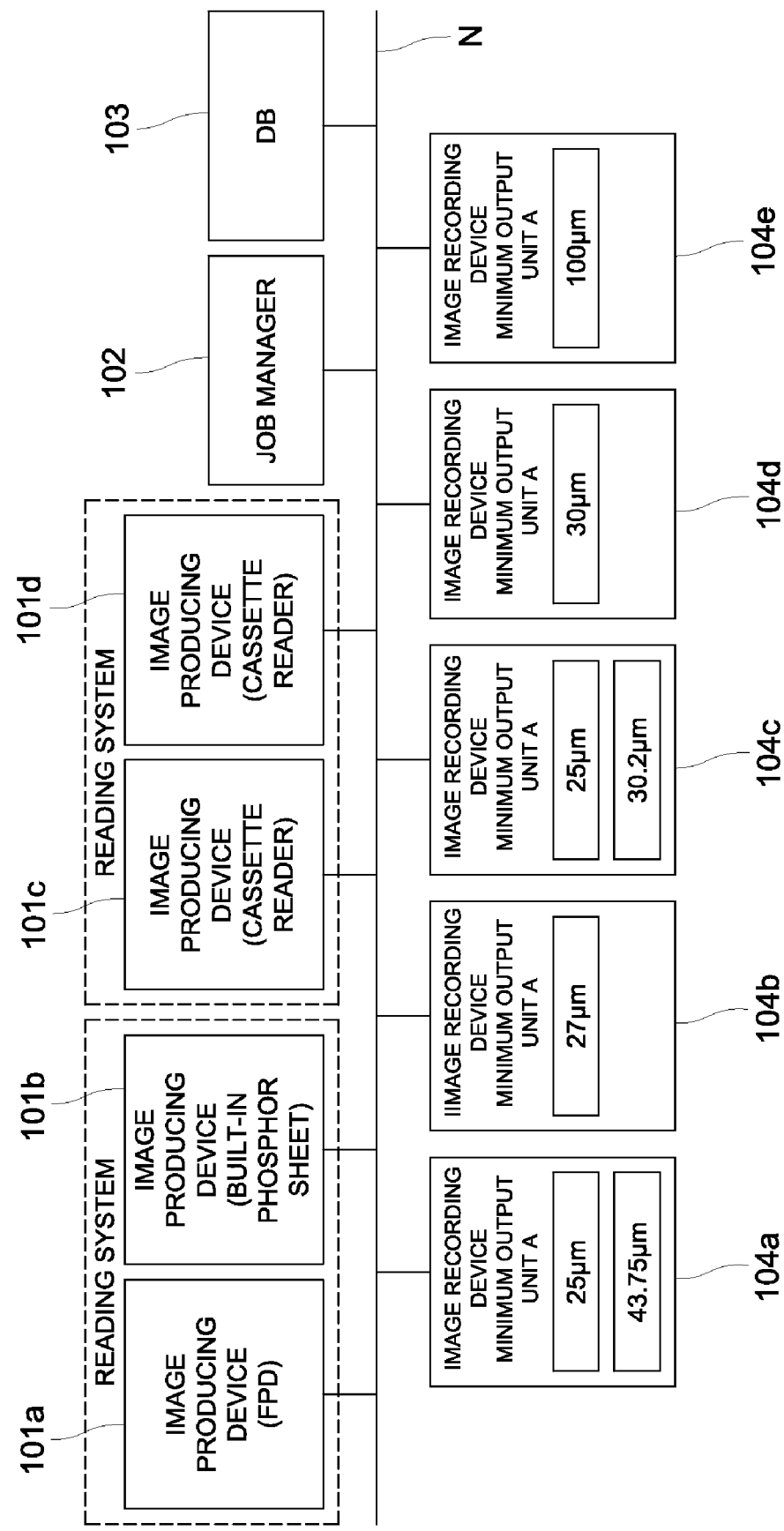
FIG. 14 shows a brief configuration of a digital radiation image radiographing system embodied in the present invention as the second embodiment.

FIG. 14 shows the structure of digital radiation image radiographing system in the present embodiment.

As shown in FIG. 14, the digital radiation image radiographing system 100 is composed of image generating apparatuses 101a-101d, JOB manager 102, DB (Data Base) 103, image recording apparatuses 104a-104c and image display apparatuses 104d and 104e. Each apparatus is constructed to be capable of conducting transmission and reception of information through network N conforming to the standards of DICOM (Digital Imaging and Communication in Medicine).

Image generating apparatuses 101a-101d are those to generate digital data of X-ray images acquired through imaging of a subject, and they are classified into image generating apparatuses 101a and 101b of an radiographing system that conducts imaging operations and generating operations for X-ray images on the same apparatus and image generating apparatuses 101c and 101d of a reading system that is constructed separately from the radiographing apparatus, and reads X-ray images recording on a portable image detector to generate X-ray image data.

The image generating apparatuses 101a and 101b are equipped with an imaging device composed of an X-ray tube and an image detector (FPD or a phosphor sheet) and with an image generating device that reads X-ray images recorded on the image detector and generates image data, and conduct imaging operations and image generating operations. The image generating device functions as a digital image detector that digitizes X-ray images.

On the other hand, in the case of image generating apparatuses 101c and 101d of the reading system, an image generating device (that functions as a digital image detector) only is provided, and imaging operations are conducted by an radiographing apparatus constructed separately by the use of a portable image detector such as a cassette. The image generating apparatuses 101c and 101d conduct reading operations for X-ray images recorded on a cassette through imaging operations.

The phase contrast radiographing method and the X-ray image generating method are common to all of the image generating apparatuses 101a-101d. Detailed explanation for the radiographing method will be given later.

JOB manager 102 is one that regulates and controls a flow of X-ray images in digital radiation image radiographing system 100. It further conducts output regulation in the case of outputting X-ray images by each outputting apparatus of image recording apparatuses 104a-104c or of image displaying apparatuses 104d and 104e.

Further, the JOB manager 102 receives information of instruction for imaging designated by a doctor concerning imaging which is called imaging order information from unillustrated HIS (Hospital Information System) or RIS (Radiology Information System), and stores the information. Based on this imaging order information, X-ray images taken through imaging are controlled by the JOB manager 102. For example, since the imaging order information includes patient information (a name, an age and the distinction of sex) concerning a subject (patient) to be imaged and imaging information (a region to be imaged, an imaging direction and an radiographing method) concerning imaging, the JOB manager 102 retrieves the imaging order information corresponding to X-ray images, and causes patient information and imaging information included in the imaging order information to accompany the X-ray images. It further causes image generating information (minimum generation unit in the case of image generation, an amount of image data and others) in the course of image generation in image generating apparatuses 101a-101d to accompany X-ray images. Each X-ray image can be discriminated individually based on accompanying information.

Figures 15, 16:
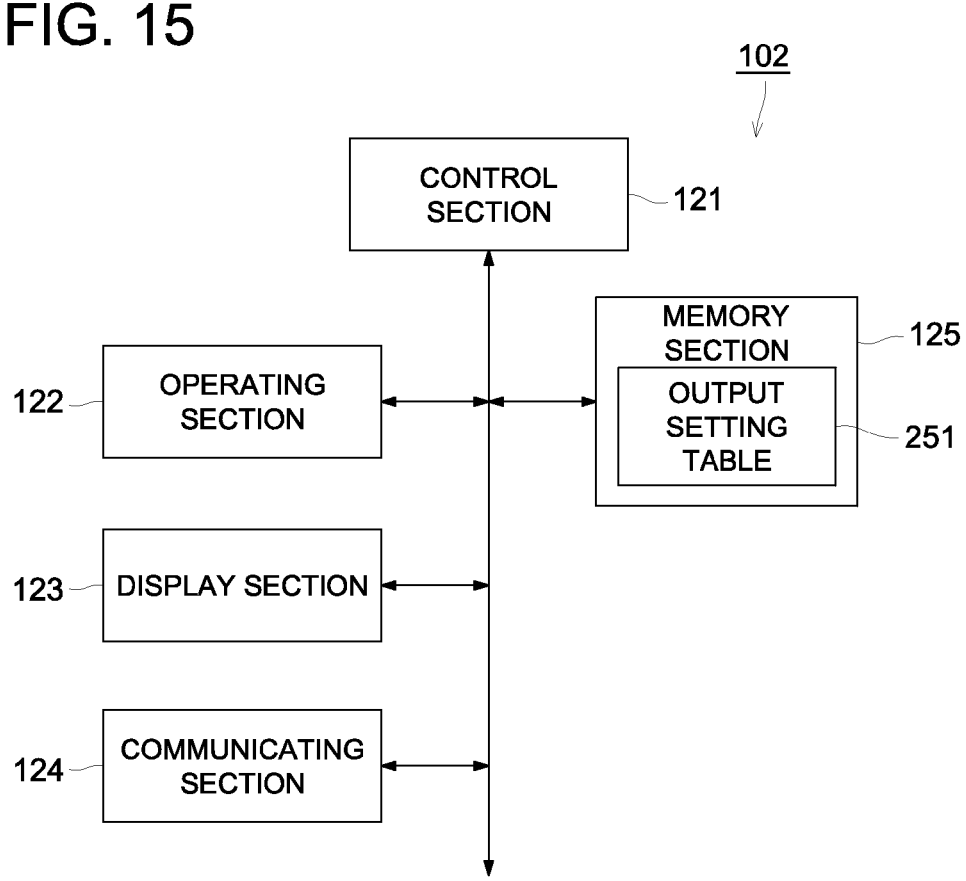
FIG. 15 shows an internal configuration of a JOB manager shown in FIG. 14.
FIG. 16 shows an example of output setting table in which output setting information of each of output apparatuses shown in FIG. 14 are stored.

FIG. 15 shows an internal structure of the JOB manager 102.

As shown in FIG. 15, the JOB manager 102 is composed of control section 121, operation section 122, display section 123, communication section and storage section 125.

The control section 121 is composed of CPU (Central Processing Unit) and RAM (Random Access Memory), and it reads out various control programs from the storage section 125, and conducts centralized control for various calculations and operations of respective sections 122-125 through cooperation with the program thus read out.

The operation section 122 is equipped with a key board and a mouse, and generates operation signals corresponding to the operations of these operators, and outputs them to the control section 121.

The display section 123 is equipped with a display such as LCD (Liquid Crystal Display), and it displays various types of display information such as various types of operation screens and results of processing by the control section 121.

The communication section 124 is equipped with an interface for communication such as a network interface card, and it conducts transmission and reception of information with each equipment on network N.

The storage section 125 stores data including various types of control programs, parameters necessary for practice of programs, and results of processing by the control section 121.

The storage section 125 further stores output setting table 251.

The output setting table 251 is a table for controlling output setting information in an output apparatus included in digital radiation image radiographing system 100, namely, in image recording apparatuses 104a-104c and image display apparatuses 104d and 104e.

For example, various types of setting information such as a form of output of an output apparatus (film recording or monitor display) and minimum output unit A that can be outputted (which is also called minimum control unit in the course of outputting) (unit μm) are stored in the output setting table 251, for each output apparatuses ID (104a-104d) attached inherently on each output apparatus, as shown in FIG. 16. In this case, the minimum output unit A means a minimum constituting unit that constitutes an output image in the case of outputting an X-ray image, and it means a pixel size and a writing pitch size specifically. Incidentally, when a single output apparatus can conduct outputting with plural minimum output units, information of setting plural minimum output units is stored. These pieces of information for setting output are registered and established, each time the output apparatus is introduced newly into digital radiation image radiographing system 100.

DB 103 is composed of a large capacity memory, and it stores X-ray images generated through imaging. Each X-ray image is converted into a database by accompanying information that is created by JOB manager 102, to be controlled.

Image recording apparatuses 104a-104c and image display apparatuses 104d and 104e are those conducting output processing for X-ray images, and the image recording apparatuses 104a-104c record X-ray images on a film, while, the image display apparatuses 104d and 104e display X-ray images on a monitor. Hereafter, these apparatuses are generically called output apparatuses 104a-104e.

Each of output apparatuses 104a-104e has a minimum output unit capable of being outputted. When an X-ray image to be outputted and its output instruction information are inputted by JOB manager 102, output apparatuses 104a-104e conduct output processing for X-ray images inputted complying with the output instruction information. The output instruction information includes a minimum output unit to be applied in the case of outputting, an output method by that minimum output unit, film sizes and other output conditions. Each of output apparatuses 104a-104e allots signal values (pixel values) for each minimum generation unit of inputted X-ray image to each minimum generation unit designated complying with a designated output method, and composes an output image composed of minimum output units again, to conduct image output for the outputted image. Incidentally, it is also possible to employ a framework wherein processing to compose output images again is conducted in JOB manager 102 to distribute them to output apparatuses 104a-104e, and the output apparatuses 104a-104e conduct only processing to output the output images distributed from the JOB manager 102.

Next, operations of the aforesaid digital radiation image radiographing system 100.

With respect to a phase contrast imaging conducted in image generation apparatuses 101a and 101b of the radiographing system, it is basically the same as an occasion in the First Embodiment, and an explanation for the phase contrast imaging will be omitted accordingly.

When enlarged image data with high image quality are generated in image generation apparatuses 101a-101d, image generation information such as minimum generation units S (which is also called minimum control unit in the case of reading) and magnifying power M are caused to accompany the enlarged image, in each of image generation apparatuses 101a-101d.

Since reading processing is conducted immediately after imaging and data are generated, in the case of image generation apparatuses 101a and 101b of the radiographing system, minimum generation unit S and magnifying power M are detected automatically on the image generation apparatuses 101a and 101b side, and its information is written on a header area for the enlarged image. With respect to magnifying power M, it is possible to employ either a framework wherein information of the magnifying power is inputted by a cameraman, or a framework wherein the magnifying power M is automatically calculated in image generation apparatuses 101a and 102b, provided that the framework can detect a subject position and a position of image detector 12 on the image generation apparatuses 101a and 101b side.

Since a cameraman needs to load a cassette on which an enlarged image is recorded in image generation apparatuses 101c and 101d, after imaging, in image generation apparatuses 101c and 101d of a reading system, a framework wherein minimum generation unit S and magnifying power M are inputted by an operator in that case is employed, and information of the minimum generation unit S and magnifying power M inputted at image generation apparatuses 101c and 101d are written on a header area of the enlarged image thus read.

Data of enlarged images which are accompanied by image generation information such as minimum generation unit S and magnifying power M are transmitted to JOB manager 102. In the JOB manager 102, when data of enlarged images are received from image generation apparatuses 101a-101d, accompanying information based on imaging order information is caused to accompany the enlarged image, and is preserved in DB 103.

After that, in the JOB manager 102, output control processing to distribute enlarged images preserved in DB 103 to output apparatuses 104a-104e is practiced.

Figure 17:
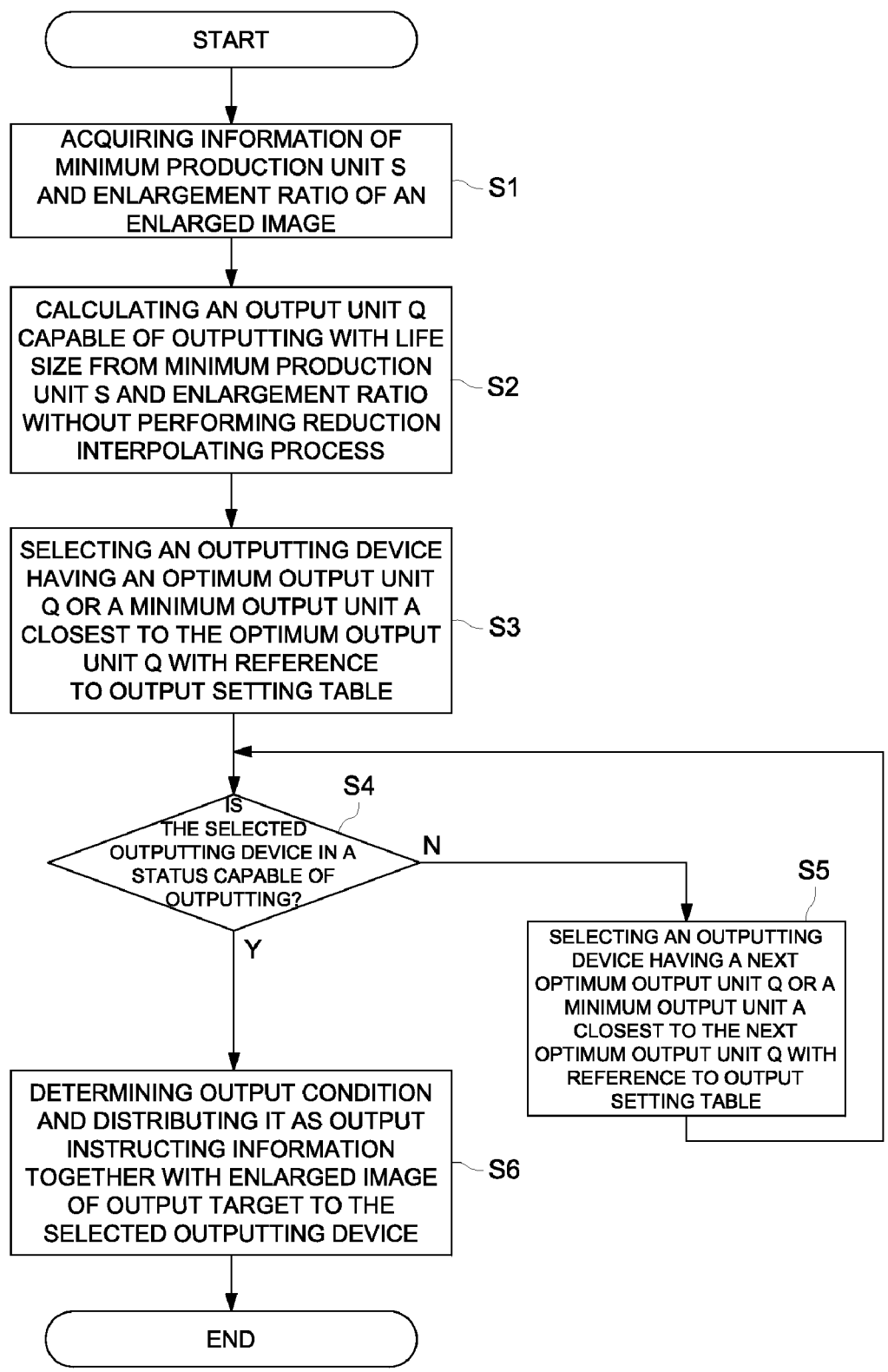
FIG. 17 shows a flowchart for explaining a flow of output controlling operations to be implemented by the JOB manager.

A flow of the output control processing will be explained as follows, referring to FIG. 17. Incidentally, the output control processing is software processing realized by cooperation with processing programs stored in control section 121 and storage section 125.

First, information accompanying the enlarged image data received is referred to, and information of minimum generation unit S and magnifying power M is acquired (step S1). Then, from these minimum generation unit S and magnifying power M, optimum generation unit Q capable of outputting at a life size is calculated, without conducting minifying interpolation processing. Namely, optimum output unit Q that satisfies the following expression (5) is obtained (step S2).

$$Q=S/M \quad (5)$$

When a signal value of minimum generation unit S is made to be a signal value of minimum output unit A on a basis of one-to-one correspondence between minimum generation unit S and minimum output unit A, minifying interpolation processing turns out to be unnecessary. This also applies to an occasion where a signal value is caused to correspond to aggregate nA of minimum output unit A (n can take a value of a square of an integer). For example, if magnifying power M is 1.75, minimum generation unit S is 43.75 (μm) and minimum output unit A is 12.5 (μm), a single pixel of S=43.75 (μm) in the case of image generation results in corresponding to an amount equivalent to 4 pixels (lengthwise: 2 pixels× breadthwise: 2 pixels) each being of A=12.5 (μm) on a one-to-one correspondence basis. in the case of outputting.

Therefore, it is possible to output a life-size enlarged image without deteriorating image quality, while keeping edge effects, by conducting output with an output unit (minimum output unit A or its aggregate nA) capable of outputting enlarged images at a size that is the same as or close to the life-size one, even when signal values are allotted as stated above.

Next, output setting table 251 is referred to, and there are selected output apparatuses 104a-104e wherein minimum output unit A can output with an output unit that is desired optimum output unit Q or is closest to the desired optimum output unit Q, and S>A is satisfied (step S3). In this case, an output device of minimum output unit A that can output with optimum output unit Q is selected preferentially, and then, the selection is made preferentially, from an output device of minimum output unit A that can output with an output unit closest to optimum output unit Q. Incidentally, the relationship of S>A is required by the purpose to output life-size enlarged images. Further, the minimum output unit A capable of outputting with optimum output unit Q (or an output unit closest to it) means that an occasion wherein output is possible with minimum output unit A itself and an occasion output is possible by aggregate nA of minimum output unit A are included.

For example, when minimum generation unit S is 43.75 (μm), magnifying power M is 1.75 and output to a film is instructed, the optimum output unit Q is obtained from the expression (5) above to be 25 (μm). In the example of output setting table 251 shown in FIG. 16, there exist two output apparatuses including output apparatuses 104a and 104c, wherein minimum output unit A is the same as optimum output unit 25 (μm) in the case of outputting on a film. Therefore, any one of the output apparatuses 104a and 104c is selected The selection of the output apparatus may either be on an optional basis, or on other conditions such as a film size that makes it possible for the output apparatus to output.

Then, the selected output apparatuses 104a-104e are discriminated whether they are in the state to be capable of outputting or not (step S4), and when they are not in the state to be capable of outputting (step S4; N), an output apparatus having minimum output unit A that can output with optimum output unit Q or with an output unit closest to the optimum output unit Q is selected (Step S5).

In the aforesaid example, even when the output apparatus 104a among output apparatuses 104a and 104c is selected, if the status information such as that the output apparatus 104a is not turned on or that a large amount of image data to be outputted are waiting for outputting, the output apparatus 104a is judged to be in the state where output is impossible, and an output apparatus that is the same as or is the closest to optimum output unit Q is selected next from other output apparatuses 104b-104e excluding the output apparatus 104a. In this example, since the output apparatus 104c has minimum output unit A (25 μm) identical to optimum output unit Q, output apparatus 104c is selected.

Further, when both of output apparatuses 104a and 104c each having minimum output unit A identical to optimum output unit 25 (μm) are impossible to output, output apparatus 104b having minimum output unit A of 27 (μm) close next to optimum output unit 25 (μm) is selected preferentially. If signal values of minimum generation unit s 43.75 (μm) are allotted to one pixel having a size of minimum output unit A 27 (μm) on a one-to-one correspondence basis, its output image is one enlarged from a life-size one by 1.08 times as shown in FIG. 18, and it is not a life-size (magnifying power 1.0) one. However, if the magnifying power is as small as this, an image can be used for X-ray interpretation as a life-size one substantially without a problem, and therefore, the selection is made preferentially under the condition that an output close to optimum output unit Q is possible.

In other words, if minimum generation unit S is 43.75 (μm), magnifying power M is 1.75 and output is made on a film in the case of output setting shown in FIG. 16, the selection is made preferentially in the order of 25 (μm) of output apparatus 104a or 104c, 27 (μm) of output apparatus 104b, 30.2 (μm) of output apparatus 104c and 43.75 (μm) of output apparatus 104a.

If output apparatuses 104a-104c each being capable of outputting are selected as stated above (step S4; Y), output conditions are determined on control section 121, and output instruction information showing the output conditions is generated to be distributed to the aforesaid selected output apparatuses 104a-104c together with data of enlarged images to be outputted (step S6).

The output condition includes a condition in the case of allotting signal values of minimum generation unit S to minimum output unit A, namely, a condition to allot signal values in one unit of minimum generation unit S to one unit of minimum output unit A (or its aggregate nA) by causing them to correspond on a basis of one-to-one correspondence. When allotting with an aggregate unit, information of minimum output unit number n constituting the aggregate nA is also included. In output apparatuses 104a-104e, it is possible to output at a life-size dimension or at a dimension close to the life-size dimension without conducting minifying interpolation processing, because images to be outputted are generated from enlarged images in accordance with the output instruction information, and outputting of them is conducted.

Further, when outputting by plural minimum output units A is possible in the selected output apparatuses 104a-104e, a condition showing which minimum output unit A should be used for outputting is included in the output conditions. In addition, if there is a film size or the like designated by a cameraman, the output condition of that size information is also included in the output conditions.

In output apparatuses 104a-104e where an enlarged image and its output instruction information are received from JOB manager 102, output operations for the enlarged image to be outputted are carried out in accordance with the output instruction information in the aforesaid way.

As stated above, the present embodiment makes it possible to control so that image outputting may be practiced by the output apparatus that conforms to minimum generation unit S and magnifying power M, in spite of a digital radiation image radiographing system equipped with plural output apparatuses each having different minimum output unit A. Owing to this, an enlarged image which is edge-emphasized by phase contrast imaging and has excellent visibility and high image quality can be outputted at a life-size dimension or a dimension close to the life-size dimension, without conducting minifying interpolation processing, and X-ray images which are optimum for X-ray interpretation can be offered.

Further, even when one of output apparatuses 104a-104e is selected, if the selected one of output apparatuses 104a-104e is not under the condition to be capable of outputting, selection is made again from other output apparatuses 104a-104e. Thus, it is possible to distribute images to be outputted, while considering the conditions of plural output apparatuses 104a-104e.

In addition, when a plurality of minimum output units A can be applied in the selected output apparatuses 104a-104e, it is possible to output of optimum output unit Q by designating the feasible minimum output unit A.

The invention claimed is:

1. A radiation image radiographing system, comprising:
   an X-ray tube, having a focal point, to irradiate a radiographic subject with X-rays; and
   a digital detector, having a minimum control unit, to detect X-rays having passed through the radiographic subject based on the minimum control unit,
   wherein respective positions of the X-ray tube, the radiographic subject, and the digital detector are arranged to perform a phase contrast radiography, and
   wherein when D (μm) represents a focal point size of the X-ray tube, S (μm) represents the minimum control unit of the digital detector, R1 (m) represents a distance from the focal point of the X-ray tube to the radiographic subject,
   R2 (m) represents a distance from the radiographic subject to the digital detector, M represents an enlargement ratio obtained by the formula (M = (R1 + R2)/R1), and E represents an edge enhancement caused by the phase contrast radiography, the digital radiation image radiographing system satisfies the formula $(D \geq (2S-E)/(M-1))$.

2. The radiation image radiographing system described in claim 1, further comprising:
   an image outputting device, having a minimum control unit A (μm), to output an X-ray image corresponding to the X-rays detected by the digital detector based on the minimum control unit A,
   wherein the minimum control unit S and the minimum control unit A are predetermined to satisfy the formula (S>A), and the minimum control unit S is matched with an aggregation nA of n pieces of the minimum control unit A so as to output the X-ray image.

3. The radiation image radiographing system described in claim 2, further comprising:
   a plurality of image outputting devices as the image outputting device;
   a selecting section to acquire information about respective minimum control units A of the plurality of image outputting devices and to select an image outputting device having a minimum control unit A equal to the value of (S/M) or closest to the value of (S/M); and
   an output control section to allot a signal value for each one minimum control unit S as a signal value for each one minimum control unit A or each aggregation nA of the minimum control unit A of the selected image outputting device and to control the selected image outputting device to output the X-ray image.

4. The radiation image radiographing system described in claim 3, wherein the selecting section selects an image outputting device having a minimum control unit A closest to the value of (S/M) when an image outputting device having a minimum control unit A equal to the value of (S/M) is not available.

5. The radiation image radiographing system described in claim 3, wherein when at least one of the plurality of image outputting devices is capable of outputting with a plurality of minimum control units A, the selecting section selects an image outputting device having a minimum control unit A equal to the value of (S/M) among the plurality of minimum control units A, and the output control section controls the selected image outputting device to output the X-ray image with the minimum control unit A equal to the value of (S/M) among the plurality of minimum control units A.

6. The radiation image radiographing system described in claim 2, wherein when (S=MA), (n=1), where n represents the number of the minimum control unit A in the aggregation nA.

7. A radiation image radiographing system, comprising:
   an X-ray tube, having a focal point, to irradiate a radiographic subject with X-rays; and
   a digital detector, having a minimum control unit, to detect X-rays having passed through the radiographic subject based on the minimum control unit,
   wherein positions of the X-ray tube, the radiographic subject, and the digital detector are arranged to perform a phase contrast radiography, and
   wherein when D (μm) represents a focal point size of the X-ray tube, S (μm) represents the minimum control unit of the digital detector, R1 (m) represents a distance from the focal point of the X-ray tube to the radiographic subject,
R2 (m) represents a distance from the radiographic subject to the digital detector, M represents an enlargement ratio obtained by the formula (M=(R1+R2)/R1), and E represents an edge enhancement caused by the phase contrast radiography, the digital radiation image radiographing system satisfies the formula (D≧2S/(M−1)).

8. The radiation image radiographing system described in claim 7, further comprising:
   an image outputting device, having a minimum control unit A (μm), to output an X-ray image corresponding to the X-rays detected by the digital detector based on the minimum control unit A,
   wherein the minimum control unit S and the minimum control unit A are predetermined to satisfy the formula (S>A), and the minimum control unit S is matched with an aggregation nA of n pieces of the minimum control unit A so as to output the X-ray image.

9. The radiation image radiographing system described in claim 8, further comprising:
   a plurality of image outputting devices as the image outputting device;
   a selecting section to acquire information about respective minimum control units A of the plurality of image outputting devices and to select an image outputting device having a minimum control unit A equal to the value of (S/M) or closest to the value of (S/M); and
   an output control section to allot a signal value for each one minimum control unit S as a signal value for each one minimum control unit A or each aggregation nA of the minimum control unit A of the selected image outputting device and to control the selected image outputting device to output the X-ray image.

10. The radiation image radiographing system described in claim 9, wherein the selecting section selects an image outputting device having a minimum control unit A closest to the value of (S/M) when an image outputting device having a minimum control unit A equal to the value of (S/M) is not available.

11. The radiation image radiographing system described in claim 9, wherein when at least one of the plurality of image outputting devices is capable of outputting with a plurality of minimum control units A, the selecting section selects an image outputting device having a minimum control unit A equal to the value of (S/M) among the plurality of minimum control units A, and the output control section controls the selected image outputting device to output the X-ray image with the minimum control unit A equal to the value of (S/M) among the plurality of minimum control units A.

12. The radiation image radiographing system described in claim 8, wherein when (S=MA), (n=1), where n represents the number of the minimum control unit A in the aggregation nA.

* * * * *